United States Patent [19]

Ehrnford

[11] 4,381,918
[45] May 3, 1983

[54] METHOD OF PRODUCING A COMPOSITE RESIN, PREFERABLY FOR USE AS A DENTAL MATERIAL

[76] Inventor: Lars E. M. Ehrnford, 31 Sanekullavagen, 217 14 Malmo, Sweden

[21] Appl. No.: 302,995

[22] Filed: Sep. 17, 1981

Related U.S. Application Data

[63] Continuation-in-part of Ser. No. 226,636, Jan. 21, 1981, which is a continuation of Ser. No. 777,909, Mar. 15, 1977, abandoned.

[30] Foreign Application Priority Data

Mar. 16, 1976 [SE] Sweden .............................. 7603313

[51] Int. Cl.$^3$ .............................................. A61K 6/08
[52] U.S. Cl. ...................................... 433/199; 106/35; 260/998.11; 264/16; 264/19; 523/115; 523/116; 523/117; 433/201; 433/202; 433/212; 433/222; 433/228
[58] Field of Search ............... 433/199, 201, 202, 228, 433/212; 523/115, 116; 264/16, 19; 260/998.11; 106/35

[56] References Cited

U.S. PATENT DOCUMENTS

| | | | |
|---|---|---|---|
| 2,106,744 | 2/1938 | Hood et al. | 106/36.1 |
| 3,036,980 | 5/1962 | Dunham et al. | 260/31.4 |
| 3,066,112 | 11/1962 | Bowen | 260/41 |
| 3,328,230 | 6/1967 | Levecque et al. | 428/296 |
| 3,428,595 | 2/1969 | Tsukada et al. | 260/41 |
| 3,549,524 | 12/1970 | Haller | 210/31 |
| 3,955,024 | 5/1976 | Goldman et al. | 428/268 |
| 4,055,268 | 10/1977 | Barthel | 428/296 |
| 4,215,033 | 7/1980 | Bowen | 260/42.15 |
| 4,217,264 | 8/1980 | Mabie et al. | 433/228 |
| 4,222,128 | 9/1980 | Tomonaga et al. | 3/1.9 |
| 4,234,310 | 11/1980 | Leuthard | 433/228 |
| 4,321,042 | 3/1982 | Scheicher | 433/201 |

FOREIGN PATENT DOCUMENTS

| | | |
|---|---|---|
| 2743168 | 4/1980 | Fed. Rep. of Germany . |
| 849833 | 9/1960 | United Kingdom . |
| 1066794 | 4/1967 | United Kingdom . |
| 1576537 | 10/1980 | United Kingdom . |

*Primary Examiner*—Lorenzo B. Hayes
*Attorney, Agent, or Firm*—Bacon & Thomas

[57] ABSTRACT

A method of producing a composite of organic resin and inorganic porous particles, preferably for use as a dental restoration material, which comprises impregnating porous inorganic particles with an at least partially hardenable resin material, compressing or otherwise applying pressure in such a way that the particles contact each other and the pressure in the resin is equalized by viscous flow of excess resin through the pores of the inorganic particles, bonding together by hardening of at least a portion of the hardenable resin material, thereby forming a resin structure including a contiguous inorganic phase.

37 Claims, 1 Drawing Figure

0,01mm

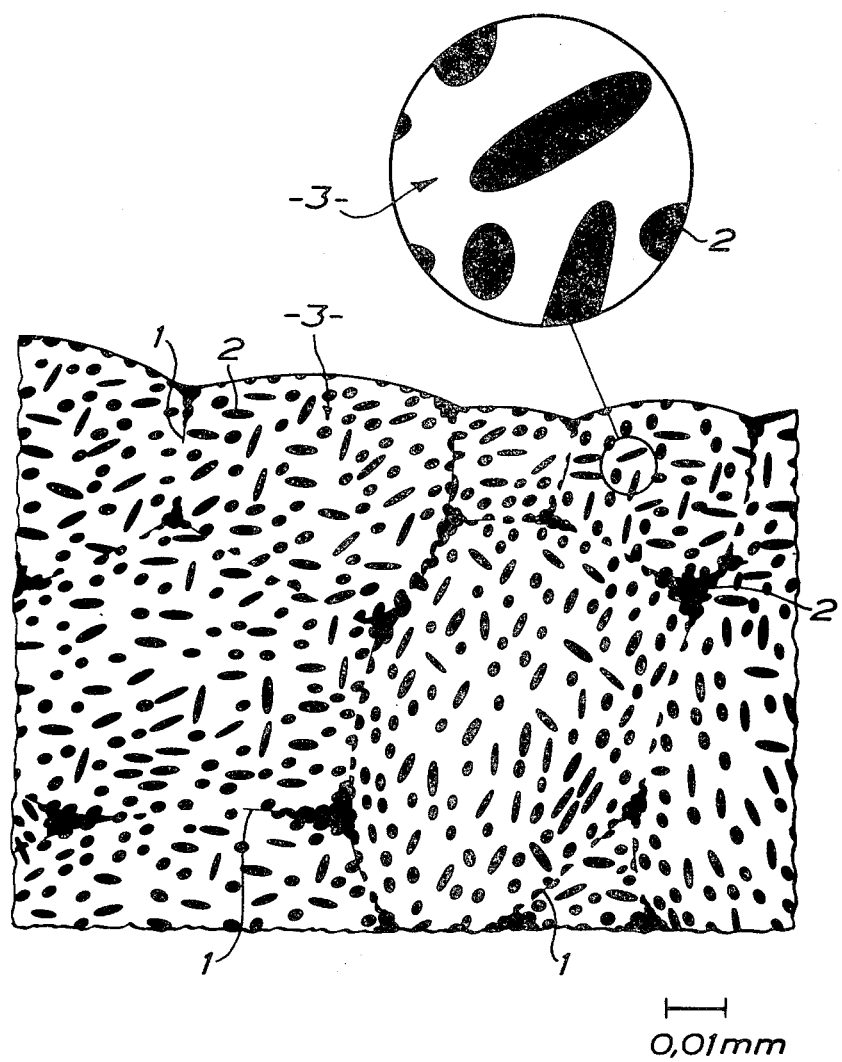
0,01mm

METHOD OF PRODUCING A COMPOSITE RESIN, PREFERABLY FOR USE AS A DENTAL MATERIAL

CROSS-REFERENCE TO RELATED APPLICATIONS

This application is a continuation-in-part of copending application Ser. No. 226,636, filed Jan. 21, 1981, which is a continuation of U.S. application Ser. No. 777,909, filed Mar. 15, 1977, now abandoned.

BACKGROUND OF THE INVENTION

The present invention relates to a method of producing composite resins, preferably for use as a dental material, including dental filling and facing materials, luting cements, crown and bridge materials, denture and artificial-teeth materials.

For the production of composite materials it is known to bind ceramic particles by means of a resin. Generally, one proceeds from a paste or putty-like mixture of hardenable monomer (organic liquid resin) and solid ceramic particles. The ceramic particles are bonded when the monomer hardens. This technique requires an excess amount of monomer, which results in the particles being separate at a substantial distance from each other in the hardened structure. The resin component will therefore negatively affect the properties of the composite material, at least as far as strength, rigidness and surface structure are concerned. Other properties, such as the thermal and viscoelastic properties, color stability, surface smoothness and the shrinkage at hardening are also affected thereby. A dental restorative composite resin of this kind comprising a blend of liquid polymerizable organic binder and a solid inorganic filler is described in U.S. Pat. No. 3,006,112 to Bowen.

SUMMARY OF THE INVENTION

The object of the present invention is to eliminate these drawbacks in the prior art and to provide a method and composition which substantially improve the properties of composite resins in these respects. According to the invention, this method of production is characterized in that a mass, comprising porous inorganic particles which are completely or partially impregnated with at least a partially hardenable resin material, is compressed or otherwise applied in such a way that the particles contact each other and pressure in the liquid resin is equalized by viscous flow in the pores of the inorganic particles. The particles are bonded together by hardening of at least a portion of the hardenable resin material thereby forming a resin structure including a contiguous inorganic phase.

The composite resin produced according to this method also provides advantageous manipulative properties during production of dental restorations.

The method according to the present invention also permits use of resins with better properties than those which have been previously available, especially since resins having a higher average molecular weight and viscosity may now be used. It is possible to achieve a composite with less resin between the particles than previously known.

BRIEF DESCRIPTION OF THE DRAWING

The composite resin is illustrated in the FIGURE.

DESCRIPTION OF THE PREFERRED EMBODIMENTS

The invention will now be described in further detail with reference to the accompanying drawing in which the only FIGURE illustrates, in a one thousand fold enlargement, a portion of a composite resin produced by way of the method according to the present invention.

The composite resin illustrated in the FIGURE was obtained by the method of the present invention which comprises compressing a mass of porous inorganic particles 1 which are completely or partially impregnated with an at least partially hardenable resin material 2, in such a way that the particles contact each other and are then bonded together by hardening of at least a portion of the hardenable resin material thereby forming a resin structure including a contiguous inorganic phase.

In the method according to the present invention, various types of porous inorganic particles 1 may be used, such as particles of a rigid three-dimensional network of inorganic fibres sintered together at those points where the fibres contact each other. It is particularly advantageous if the fibres have a diameter of less than 4 microns, and preferably a diameter of from 1 to 3 microns. The extremely fine diameter fibres will give a structure that after wear will show a surface of high smoothness which is particularly advantageous for dental restorations.

The inorganic fibres having the aforementioned sizes are fused together by heating at a temperature sufficient to cause melting and complete fusing together of substantially all individual fibres at their points of contact into a network where the porosity is continuous throughout the entire network. The porosity of such a network is extensive and more pore diameters are less than 10 microns, and preferably the procedure results in a network having pore diameters of less than 2 microns. With respect to surface smoothness, it is particularly advantageous if substantially all pore diameters are less than 10 microns and preferably less than 2 microns. Such a network preferably comprises glass which has a high radiopacity to X-rays and also preferably is produced from extremely fine fibres such as those used in the following example:

A pair of square and planoparallel press plates ($12 \times 12 \times 1.5$ cm) were made of a hydraulic cement (Secar® 250, Lafarge Aluminous Cement Co. Ltd., Essex, England) in stainless steel molds. One of the flat press surfaces was provided with small projections (hemispheres) along the periphery to secure a minimum distance between the plates. The same plate was also provided with a thermocouple (Ni,Cr-Ni) with the measuring point centrally and partially exposed in the press surface. The temperature was recorded on a printer. To obtain even heating, the press plates were enclosed in a stainless steel box (wall thickness: 5 mm), just large enough to receive the two press plates. This technique made it possible to keep the temperature differences less than 10° C. within the central area ($65 \times 65$ mm) between the plates used for sintering. Fibre down (supplied by Bilson AB, Billesholm, Sweden) of A-glass type (soda lime) with a fibre diameter of $2 \pm 1$ microns was used. It was placed between the plates in the predetermined sintering area and compressed by 3 kPa, the pressure produced by the total weight of the upper press plate and the upper part of the steel box. The loaded box was placed in an electric furnace, automatically held at 800° C. When after approximately 20 minutes a temperature of 685°±5° C. was reached in the measuring point, the sintering was stopped. The box was allowed to cool down at room temperature and at approximately 300° C. it was opened and the sintered sheet was removed. Because of the spacers in the press plate, the sheet was then 775±25 microns thick.

The amount of glass-fibre down required between the plates to get the desired porosity was calculated with the use of a glass density of 2.5 g/cm³. Two degrees of porosity were used, one giving the sheet an average glass content of approximately 40% and the other approximately 56% by volume.

The sheets were crushed and ground with a porcelain mortar and pestle. The powder was sifted through a series of standard sieves (Din 4188) and the fractions were designated according to the size of the mesh openings (in microns) at the sieve where it was collected plus the next larger size. One fraction of "coarse" (250/160), two "medium" (160/100, 100/71) and one "fine" (71/40) fractions were collected. The powders were treated with 1-M hydrochloric acid for 24 hours and then washed with distilled water and acetone.

The most practical particle size distribution of the powder component of the dental filling material is such that the particles preferably have diameters of less than 250 but more than 10 microns. This, however, is dependent to some extent on the type of porous glass used and in some instances particle sizes of less than 10 microns can be used.

A silane surface treatment of about ½% by weight of the powder was added as silane (Silane A 174, Union Carbide Co., Lot 803 080 174) dissolved in acetone. The powder was allowed to dry at room temperature and was then heated at 110° C. for 45 minutes. If, when gently compacted, the powder did not permit a droplet of distilled water to penetrate within 5 minutes standing, silane treatment was considered satisfactory.

The inorganic particles content of the restoration composition should be between 40 and 90% by volume, preferably between 50 and 80% by volume. With a higher volume %, glass surface luster and hardness are improved.

The following examples are provided to show how the invention is performed in practice.

EXAMPLES

Bis-GMA (Freeman Chemical Co., Port Washington, Wi., U.S.A., Lot 124543), which is the reaction product of Bisphenol A and glycyclylmethacrylate described in U.S. Pat. No. 3,006,112, was diluted with TEGDMA (triethylene-glycol-dimethacrylate) in the proportions given in the table which follows. A photoinitiator (benzoin methyl ether, 0.8%) and a stabilized (monomethyl ether of hydroquinone, 0.008%) were added to the monomer composition. Colloidal silica (Aerosil® R 972, Degussa, Frankfurt, W. Germany) was added in various amounts as set forth in the table to increase the contents of the inorganic constituents and to adjust monomer viscosity.

The powder and liquid resins listed in Table 1 were mixed with the aid of a dental agate spatula on a glass slab. For "saturation" powder was added to the point where dry particles began to appear in the mixture thus indicating the lack of excess monomer in amounts large enough for it to impregnate more particles.

The powder resin mixtures were filled in cylindrical cavities (diameter 4 mm, depth 2 mm) in acrylic rods (4 cm long) with a square cross section (1×1 cm). For pressure application, an amalgam condenser with a flat and circular condenser point (diameter 1.8 mm) was used. The force applied was measured by supporting the acrylic rod on a simple balance.

Condensation (compression) was performed at right angles to the cavity floor. It was started at the center and the condenser point was then stepped over the surface until the latter was covered with overlapping marks. This was repeated once. The first time with a relatively low pressure to get a primary packing and a flat surface. When the maximum pressure (table 1) was applied, it was kept constant for about 1 sec. Portions giving a 1-1.5 mm thick layer of condensed material were inserted one at a time. Each layer was cured by exposure for 60-80 seconds to UV-radiation (Nuva-Lite®, L. D. Caulk Company, Canada).

TABLE 1

APPEARANCE AFTER ETCHING AND HARDNESS CHARACTERISTICS OF COMPOSITE SPECIMENS CONTAINING POROUS PARTICLES OF VARYING SIZE, DISTRIBUTION AND DENSITY.

| Composite No. | Composite formulation ||||| Specimen characteristics ||| 
|---|---|---|---|---|---|---|---|---|
| | Porous particles || TEGDMA in Bis-GMA (wt %) | Colloidal silica in liquid resin (wt %) | Mixture characteristics | Insertion methode | Microscopic appearance after etching | Hardness Mean$^x$ | $(H_v10)$ S.D.$_2$ (kp/mm²) |
| | Type | Fractions | | | | | | |
| 1 | Low density | Coarse (250/160,70%) Medium (160/100,20% 100/71,10%) | 8 | 11 | Saturated with powder | ≈15 M Pa packing pressure | Particles in contact | 209 | 9,6 |
| 2 | Low density | Coarse (250/160,70%) Fine (71/40,30%) | 8 | 11 | Saturated with powder | ≈15 M Pa packing pressure | No interparticle zones visible | 232 | 7,6 |
| 3 | Low density | Coarse (250/160,70%) Fine (71/40,30%) | 8 | 19 | Saturated with powder | ≈15 M Pa packing pressure | No interparticle zones visible | 244 | 15,1 |
| 4 | Low density | Coarse (250/160,70%) Fine (71/40,30%) | 20 | 19 | Saturated with powder | ≈15 M Pa packing pressure | No interparticle zones visible | 247 | 4,6 |
| 5 | Low density | Coarse (250/160,52%) Medium | 8 | 11 | Saturated with powder | ≈15 M Pa packing pressure | No interparticle zones visi- | 249 | 16,7 |

TABLE 1-continued

APPEARANCE AFTER ETCHING AND HARDNESS CHARACTERISTICS OF COMPOSITE SPECIMENS CONTAINING POROUS PARTICLES OF VARYING SIZE, DISTRIBUTION AND DENSITY.

| Composite No. | Composite formulation | | | | | | Specimen characteristics | | |
|---|---|---|---|---|---|---|---|---|---|
| | Porous particles | | TEGDMA in Bis-GMA (wt %) | Colloidal silica in liquid resin (wt %) | Mixture characteristics | Insertion methode | Microscopic appearance after etching | Hardness Mean$^x$ | $(H_{v10})$ S.D.$_2$ (kp/mm$^2$) |
| | Type | Fractions | | | | | | | |
| 6 | High density | (160/100,26%) Fine (71/40,22%) Coarse (250/160,52%) Medium (160/100,26%) Fine (71/40,22%) | 8 | 19 | Saturated with powder | ≈15 M Pa packing pressure | ble No interparticle zones visible | 293 | 9,0 |

$^x$All values are from 6 measurements.

While the packing pressure used is set forth in Table 1, this pressure may vary according to the particle densities. For example, particles having higher densities may require higher pressures for the same duration of time, i.e., one second, as described above.

The cavities were overfilled with an excess of approximately 0.5 mm thickness to ensure a complete removal of the oxygen inhibited surface layer during finishing of the surface. Insertion and curing were done at room temperature (22°±1° C.). Excess was removed and the specimen ground flush with the surface of the acrylic rod on carborundum paper No. 600. Subsequent polishing was then carried out on polishing linen with an aqueous suspension of corundum powder with a particle size designation of 0.3 micron.

Specimens to be etched were cut in the midplane and the exposed cross-section surface was ground. The specimen was then mounted with cold cure acrylic resin and polished as previously. The surface showing a cross-section of the specimen was etched with hydrofluoric acid (40%) for ½ hour and rinsed in distilled water.

Hardness was measured on the polished surface of the specimen with a Vicker's hardness tester (Type Z3, 2A, Zwick & Co., Einsingen, Ub Ulm/Donau, W. Germany) and was performed according to DIN 50133 with a 10 kp load. Before being tested the specimens were stored for 1 week (22°±1° C. and 50°±5% relative humidity).

Etched surfaces were studied microscopically in oblique incidental light (x 40). With this method, the resin-particle interface appeared well defined.

For testing polishability specimen surfaces were ground with aluminumoxide discs (Sof-Lex ®, medium, fine and superfine grits. 3M Co., St. Paul, Minn., U.S.A.) and then polished with a white rubber disc (Identoflex ®, type 1008, extra fine, Identoflex AG, Buchs, Switzerland), both at low speed.

For all the used formulation the technique resulted in a composite showing contact between the individual particles 1. In most cases they were brought to good intimate contact so that no interparticle zones were visible. Varying hardness number mainly reflected variations in inorganic contents.

In all the formulations the condensed material presented a firm surface which could be moulded with an amalgam condenser tip. All the surfaces produced on polishing with rubber discs showed surface gloss which tended to increase with the hardness number.

The Vicker's hardness number of the polymer corresponding to the different liquid resin compositions differed, as shown in a preliminary study, only to a minor and negligible degree. The hardness number therefore mainly reflects the porous particle concentration and the density of the individual particles 1.

The particle concentration was both as reflected in hardness number and microscopic appearance roughly the same for the different liquid resins 2 used (composite 2≧4). Nor was there a change when a "medium" particle fraction was incorporated (composite 5). There was, however, a considerable hardness increase when "high density particles" were used (composite 6).

In all liquid resins 2 the amount of diluent was small compared with what is generally used. The condensing technique was possible to perform even when the viscosity was further increased by incorporation of colloidal silica. This offers the choice of one or both of two possibilities, first to use a monomer with a higher average molecular weight than that which is commonly used and, second, to increase the concentration of the inorganic component by incorporation of a fraction of particles, fine enough to penetrate the porous fiber-network. For the latter purpose particles of both colloidal and noncolloidal sizes, and preferably of high radiopacity, could be used.

Reduced shrinkage on polymerization and reduced tendency for color shift may be achieved for e.g. Bis-GMA based monomers, which have higher average molecular weight (and thereby also higher viscosity) than the conventional monomers generally used. Such an increase in molecular weight could be achieved by changing the amount and molecular size of diluent and/or by incorporation of molecules even larger than Bis-GMA. Decreased shrinkage during polymerization will result in less build-up of internal stresses and in reduced void formation. Mechanical strength will also be improved and the tendency for oxygen-inhibition of polymerization decreased by an increase in average molecular weight.

It has also been shown by experiments that it is possible to condense to the desired structure powder-monomer mixtures containing substantial excess of monomer as that which is required for filling the porous particles 1, provided that the viscosity of the resin permits at least some of the excess resin to be pressed through the network, in connection with the condensation. In these cases as well as when no excess of monomer is present, the condensation may be carried out such that the main portion of the interfaces of the porous inorganic particles 1 are brought in contact, possibly in connection with substantial crushing of the surface layer of the particles. The particle crushing can be such that the particles conform to each other to such an extent that practically no interparticle spaces are left.

It is to be understood that the particles are held together not only by mechanical interlocking but also by the fact that there is an adhesion between the resin and the glass achieved by the silane (organofunctional adhesion promoter) treatment. Such treatment is known to the prior art, bus has not been able to provide sufficiently strong bonds in regular types of composites. The present invention utilizes not only this bonding but the mechanical interlocking which results from the present process. In the preferred form of the present invention, the diameter of the porosity of the channels may vary as long as the particles can be closely packed, under more or less deformation, while at the same time, the pressure in the resin is equalized by viscous flow of excess resin through the pores of the inorganic network.

Methods other than the photoinitiation utilized in the example for initiation of the polymerization reaction may also be utilized. An example of such a method is heat-curing where the free radicals necessary for polymerization are produced on the heating of a monomer containing, e.g., peroxide. In another method the mass is first divided into two portions where the first portion in addition to a thermosetting resin and inorganic constituents contains a catalyst for the thermosetting resin and the second portion contains an activator for the catalyst. Polymerization then starts on mixing of the two portions. The selection of the particular catalyst and activator and the amounts thereof are within the skill of the prior art depending upon the particular resin amount thereof employed.

In the method according to the invention, it is also possible to use porous inorganic particles 1 which only contain hardenable resin 2 in their outer portions and hardened resin 2 in their center portions.

To enhance adhesion between the inorganic constituents and the resin the former can be pretreated with an appropriate organofunctional silane coupling agent as described above. However, at least a portion of the silane can also be incorporated into the resin.

The porous inorganic particles 1 may be impregnated with thermoplastic resin 2 and compression of the mass may be carried out during heating such that the porous inorganic particles are bonded together.

The inorganic particles in the hardenable resin material 2 comprise ceramic particles of preferably aluminumoxide or siliconedioxide ($SiO_2$).

The hardenable resin 2 may substantially comprise at least one monomer and/or polymer selected from the group consisting of acrylic resin, vinyl chloride, cellulose acetate, styrene and acrylonitrile copolymer. The hardenable resin 2 may also comprise at least one acrylic monomer and/or polymer selected from the group consisting of ethyl methacrylate, ethyl acrylate and methyl methacrylate. The hardenable resin material 2 may substantially be a copolymer of an acrylic monomer and another copolymerizable monomer. The copolymerizable monomer is selected from the group consisting of styrene, butadiene, ethylene and acrylic acid.

The hardenable resin 2 comprises substantially Bis-GMA or any other derivative of Bisphenol A and hardening may be obtained through photoinitiation of a polymerization reaction.

Although the invention has been described with respect to inorganic glass particles obtained by sintering of fibers of glass or glass/crystal mixtures, the sintering may also include crystal formation. A second type of porous glass may also be used which glass can be obtained under proper conditions by leaching (acid treatment) of glasses with subliquidus miscibility gaps, as set forth in U.S. Pat. Nos. 2,106,744 and 3,549,524. From this type of glass, particles can be made which have an interconnected porosity which wholly or partially penetrates the particle.

The method according to the present invention is preferably used for making dental restorations such as fillings, facings, artificial teeth and the like. In order to provide such a dental restoration having improved mechanical, physical and esthetical properties as well as improved properties related to clinical manipulation said method is characterized in that a dental composite resin consisting essentially of porous inorganic particles which are completely or partially impregnated with an at least partially polymerizable monomer and/or polymer and which particles are condensed or otherwise applied in such a way that the particles contact each other and on polymerization are bonded together to form a resin structure including a contiguous inorganic phase.

It has in laboratory and clinical experiments been shown that with the described method it is possible to make dental restorations which possess mechanical, physical and esthetical properties which closely conform to the natural tooth structure. In addition, a negligible shrinkage on polymerization and an excellent polishability is achieved. These properties were not simultaneously obtained by the prior art process and composition.

The technique of mechanically packing and condensing a material into a tooth cavity is previously known to the dental profession in connection with dental amalgam. It has well known advantages in that it permits a close adaption of the filling material to the cavity walls and also makes it possible to make firm contacts between the restored tooth and its neighbor. Further, it makes it possible to give the restoration its final anatomic form before hardening. Thereby time-consuming and difficult finishing work with rotating instruments is avoided. These are advantages also achieved with the present method and which has previously not been possible to reach with any tooth-like restorative material.

The mechanical interlocking of the inorganic components (particularly with the exemplified type of porous element) which can be achieved during the condensation procedure results in a mass which even before curing presents a firm consistency which is a highly desirable property because clinical manipulation is facilitated. Insertion into the cavity and condensing is made easier if the material is precondensed in suitable molds to form small cakes or small pellets. Accordingly, the material can be given various degrees of coherence, with or without surface crushing of the porous particles.

The preferred embodiment is especially advantageous due to the particles' excellent capability to interlock, cling together, and be closely packed and further due to the resulting pore structure, in which pressure in the organic liquid resin is easily equalized. Condensation can therefore be performed clinically by the use of pressures of less than 20 MPa, which is essential for the clinical procedure, handleability and patient convenience. The pressures are measured as MPa and 1 kp/mm$^2$=9.80665 MPa.

Electron microscopic analysis of the sintered product of the example, where the fibre diameter was less than 4 microns, reveals that the fibres are fused together and form a glass skeleton which is crossed by a micropore system. This glass skeleton may be used as a retention element and presents a structure favorable from strength, stiffness and adhesion viewpoints. The interstices of the skeleton or network form a continuous system which renders the material capable of undergoing deep impregnation with resins, if necessary with application of reduced pressure, i.e., by applying a vacuum. It is preferably to perform the deep impregnation with larger units of the network. The impregnated large network is then cured followed by conversion, grinding to a particulate filler material. The impregnating agent (resin) of the filler (i.e., resin used to impregnate the glass skeleton) need not be the same as the agent used to form the matrix of the composite.

Besides as a particulate filler, the inorganic network may be used in large profile elements for filling, stiffening and reinforcing of dental restoration and construction materials can be as well used as an implant material. The unique features obtainable with the exemplified material having a fibre diameter of less than 4 microns, and particularly an average fibre diameter of 2 microns, when implanted in hard bone tissue has been elucidated by Ehrnford et al in a paper entitled "Bone tissue formation within a sintered microporous glass-fibre network implanted in extraction sockets in the rat," Scand. J. Dent. Res. 1980:88:130–133. Bone tissue in growth was here shown into the extremely fine cell-sized meshes which for the first time makes it possible to anchor a composite material to bone tissue.

I claim:

1. A method of producing a dental restoration composite containing an organic resin and inorganic porous particles which comprises impregnating open porous inorganic particles with an at least partially hardenable resin material, compressing in such a way that the particles contact each other and the pressure in the resin is equalized by viscous flow of excess resin through the pores of the inorganic particles, bonding together by hardening of at least a portion of the hardenable resin material thereby forming a resin structure including a polymer impregnated contiguous inorganic phase wherein the porous inorganic particles comprise a rigid three-dimensional network of inorganic fibers fused together by heating at a temperature sufficient to cause melting and complete fusing together of substantially all individual fibers at their points of contact into a network where the porosity is continuous throughout the network.

2. A method as claimed in claim 1, wherein the porous inorganic particles are brought into contact with each other such that the major part of their interface contact each other and there is mechanical interlocking of the inorganic particles.

3. The method as claimed in claim 2, characterized in that the porous inorganic particles are brought in contact with each other such that they obtain intimate contact by surface crushing.

4. The method as claimed in claim 3, wherein the particle crushing is such that the particles conform to each other to an extent that practically no interparticle spaces are left.

5. The method as claimed in claim 1, wherein the porous inorganic particles are impregnated with resin material such that excess of resin material is formed.

6. The method as claimed in claim 1, wherein the porous inorganic particles have a diameter of less than 500 microns.

7. The method as claimed in claim 6, wherein the porous inorganic particles have a diameter of less than 300 microns.

8. The method as claimed in claim 7, wherein 10–90% by weight of the porous inorganic particles have a diameter of at least 10 microns but less than 100 microns.

9. The method as claimed in claim 8, wherein 10–40% by weight of the porous inorganic particles have a diameter of at least 10 microns but less than 100 microns.

10. The method as claimed in claim 1, wherein the fibres are made of a ceramic material.

11. The method of claim 10 wherein the ceramic material is glass.

12. The method as claimed in claim 11, wherein the glass has a high density as determined by X-rays.

13. The method as claimed in claim 12, wherein the fibres in the networks have a diameter of less than 100 microns.

14. The method as claimed in claim 13, wherein the fibres have a diameter of less than 10 microns.

15. The method as claimed in claim 14, wherein the fibres have a diameter of less than 4 microns.

16. The method of claim 15 wherein the fibres have a diameter of from 1–3 microns.

17. The method as claimed in claim 1, wherein the hardenable resin material contains nonporous inorganic particles.

18. The method as claimed in claim 17, wherein the inorganic particles in the hardenable resin material comprise ceramic particles.

19. The method as claimed in claim 18, wherein the ceramic particles are of aluminumoxide or siliconedioxide (SiO$_2$).

20. The method as claimed in claim 19, wherein the ceramic particles are glass particles.

21. The method as claimed in claim 18, wherein the inorganic particles in the hardenable resin material have a high radiopacity to X-rays.

22. The method as claimed in claim 18, wherein the inorganic particles in the hardenable resin material have a size below 2 microns.

23. The method as claimed in claim 22, wherein the inorganic particles in the hardenable resin material are within the size range of 0.005 to 0.4 microns.

24. The method as claimed in claim 22, wherein the inorganic particles in the hardenable resin comprise 10 to 90 percent of the total weight of the particle resin mixture.

25. The method as claimed in claim 1, wherein the inorganic porous particles have been pretreated with an organofunctional silane adhesion promoting coupling agent whereby a chemical adhesion mechanism and a bonding mechanism involving physical penetration and interlocking contribute to the improved integrity and durability of the porous inorganic particles in combination with an organic resin.

26. The method as claimed in claim 25, wherein at least a portion of the silane bonding agent is incorporated in the resin in an amount of 0.05 to 10% by weight based on the weight of the total composition.

27. The method as claimed in claim 1, wherein the porous inorganic particles contain 30–80% by volume of inorganic substance.

28. The method as claimed in claim 17, wherein the size of the porous inorganic particles is less than 300 microns.

29. The method as claimed in claim 1 wherein the porous inorganic particles in their outer portions contain hardenable resin material and in their central portion hardened resin material.

30. The method according to claim 1 wherein the porous inorganic particles are impregnated with a thermoplastic resin and that the compression of the mass occurs during heating is such that the porous inorganic particles are bonded together.

31. The method as claimed in claim 1 or 17, wherein the hardenable resin material comprises substantially at least one monomer and/or polymer selected from the group consisting of acrylic resin, vinyl chloride, cellulose acetate, styrene and acrylonitrile copolymer.

32. The method as claimed in claim 31, wherein the hardenable resin is at least one acrylic monomer and/or polymer selected from the group consisting of ethyl methacrylate, ethyl acrylate, and methyl metacrylate.

33. The method as claimed in claim 31, wherein the hardenable resin material is substantially a copolymer of an acrylic monomer and another copolymerizable monomer.

34. The method as claimed in claim 31, wherein the hardenable resin is copolymer of an acrylic monomer and another copolymerizable monomer selected from the group consisting of styrene, butadiene, ethylene and acrylic acid.

35. The method as claimed in claim 31, wherein the hardenable resin material comprises substantially Bis-GMA or any other derivative of Bisphenol A.

36. The method as claimed in claim 1, wherein the hardening of the resin is achieved through photoinitiation of a polymerization reaction.

37. The method as claimed in claim 1, wherein a composite resin consisting essentially of porous inorganic particles which are completely or partially impregnated with an at least partially polymerizable monomer and/or polymer and which particles are condensed or otherwise applied in such a way that the particles contact each other and on polymerization are bonded together to form a resin structure including a contiguous inorganic phase.

* * * * *